(12) United States Patent
Shen

(10) Patent No.: US 11,666,427 B2
(45) Date of Patent: Jun. 6, 2023

(54) PORTABLE SIMULTANEOUS TOOTH POLISHING AND BLEACHING SYSTEM USING A FULL-CONTACT SWINGING MECHANISM

(71) Applicant: Feimo Shen, Milpitas, CA (US)

(72) Inventor: Feimo Shen, Milpitas, CA (US)

( * ) Notice: Subject to any disclaimer, the term of this patent is extended or adjusted under 35 U.S.C. 154(b) by 572 days.

(21) Appl. No.: 16/571,063

(22) Filed: Sep. 14, 2019

(65) Prior Publication Data
US 2021/0077239 A1 Mar. 18, 2021

(51) Int. Cl.
| | | |
|---|---|---|
| *A61C 19/06* | (2006.01) | |
| *A61C 17/00* | (2006.01) | |
| *A61K 8/22* | (2006.01) | |
| *A61C 1/00* | (2006.01) | |
| *A61K 8/25* | (2006.01) | |
| *A61C 17/34* | (2006.01) | |

(52) U.S. Cl.
CPC .......... *A61C 19/066* (2013.01); *A61C 1/0053* (2013.01); *A61C 17/005* (2013.01); *A61C 17/3436* (2013.01); *A61K 8/22* (2013.01); *A61K 8/25* (2013.01)

(58) Field of Classification Search
CPC ... A61C 19/066; A61C 1/0053; A61C 17/005; A61C 17/3436; A61K 8/22; A61K 8/25

USPC .......................................................... 433/82
See application file for complete search history.

(56) References Cited

U.S. PATENT DOCUMENTS

| | | | | |
|---|---|---|---|---|
| 6,409,507 | B1 * | 6/2002 | Postal | A61C 1/185 |
| | | | | 433/118 |
| 6,511,319 | B1 * | 1/2003 | Hunter | A61C 17/3436 |
| | | | | 433/125 |
| 2012/0258418 | A1 * | 10/2012 | Shen | A61C 19/066 |
| | | | | 433/29 |
| 2015/0079540 | A1 * | 3/2015 | Rek | A61C 15/048 |
| | | | | 433/118 |
| 2017/0202652 | A1 * | 7/2017 | Wang | A61C 17/005 |
| 2021/0077239 | A1 * | 3/2021 | Shen | A61C 17/005 |

* cited by examiner

*Primary Examiner* — Matthew M Nelson

(57) ABSTRACT

A portable tooth polishing and bleaching treatment system is provided for simultaneous tooth surface polishing and bleaching for use at home or in dental clinics. A full contact swinging mechanism is employed to transfer a continuously rotational input from a motor into a back-and-forth swinging movement output. The system comprises an electrically powered handpiece, a detachable swinging angle, a rubber cup, a user-specific thermoplastic gum protector, and a dual-agent mixing set consisting of a separated storage of polishing bleaching agents and an agent mixing tool. The swinging angle alone is used as a prophylaxis angle for dental clinics.

9 Claims, 15 Drawing Sheets

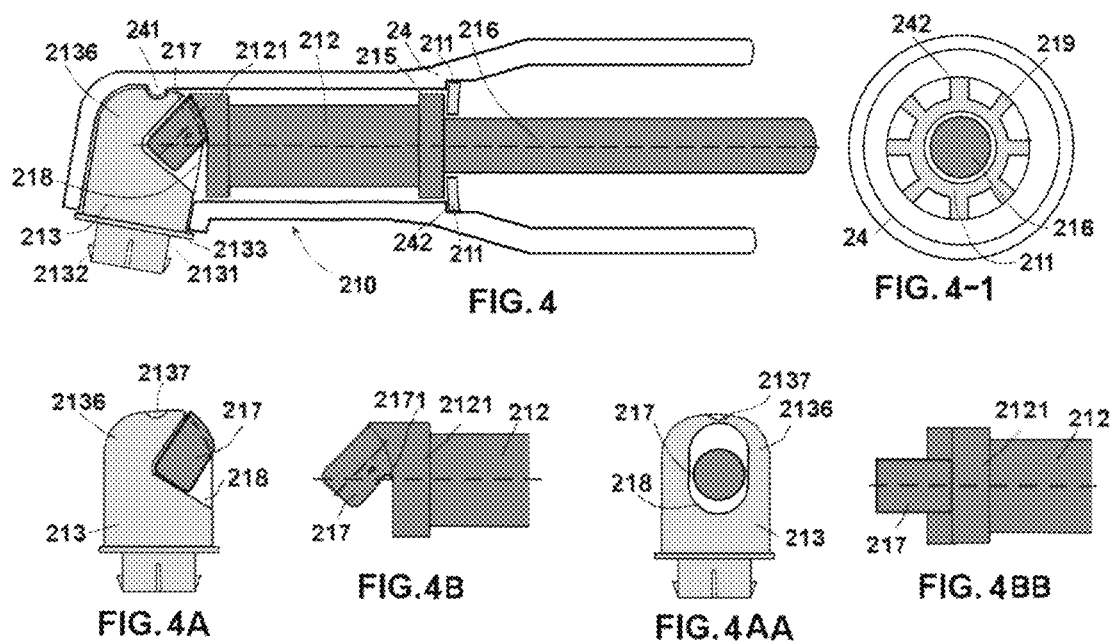

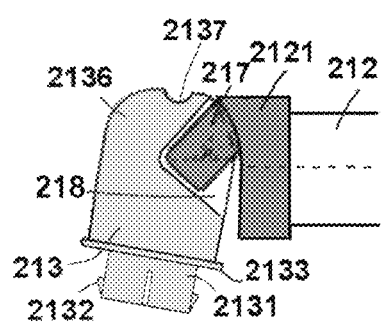 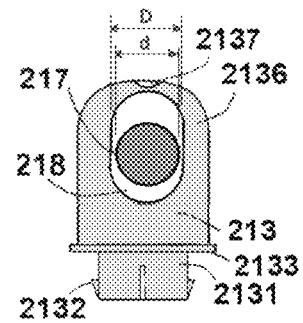 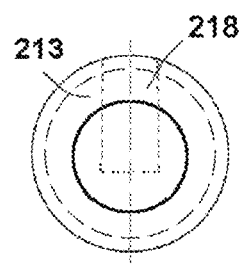
FIG. 5A      FIG. 5AC     FIG. 5AD
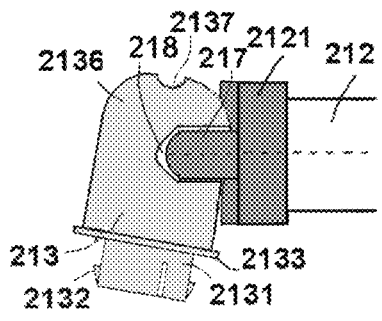 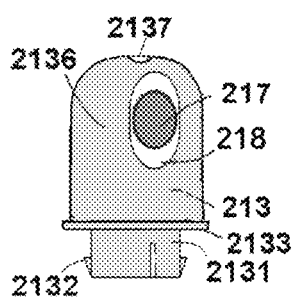 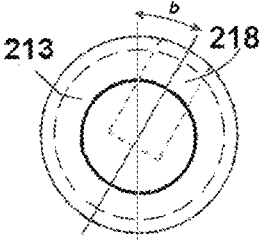
FIG. 5B      FIG. 5BC     FIG. 5BD

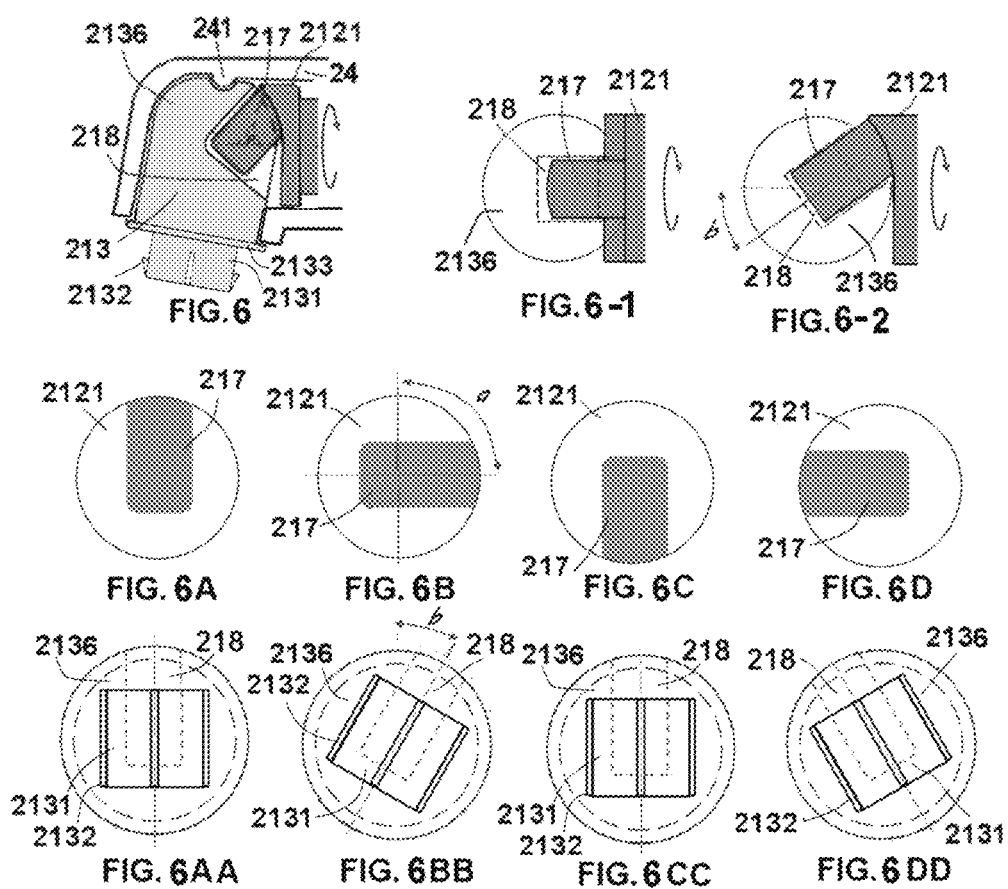

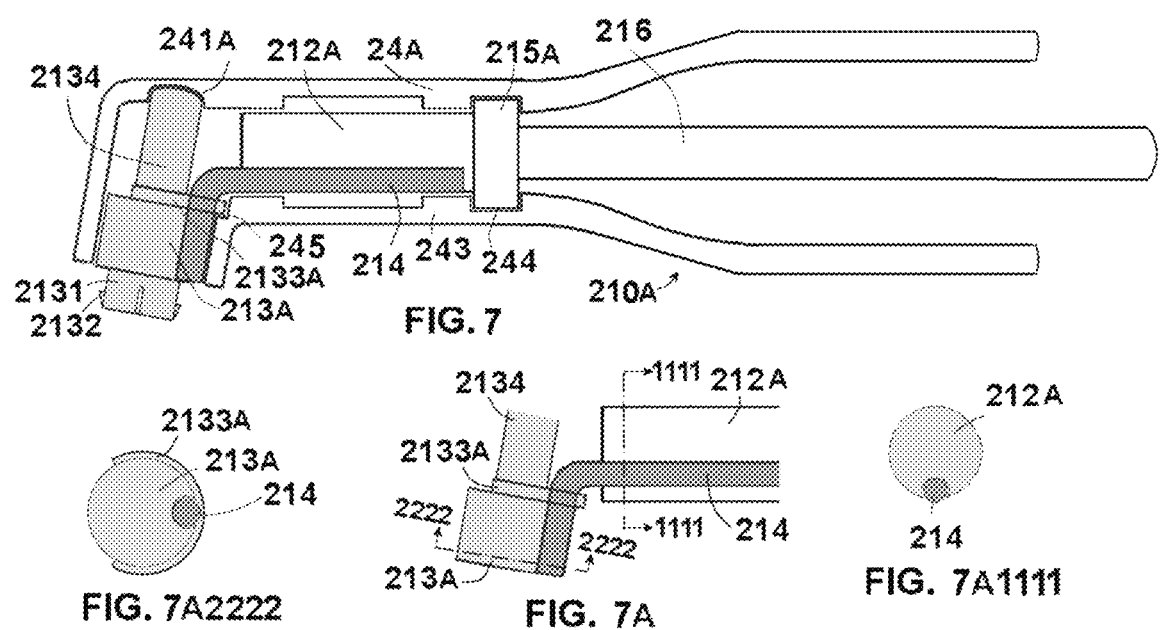

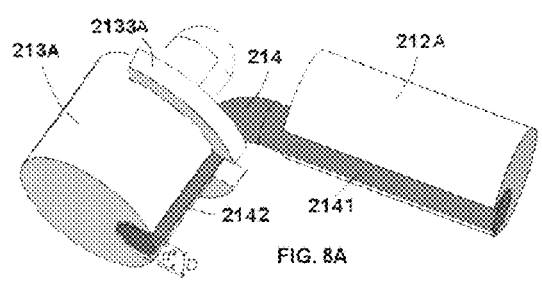
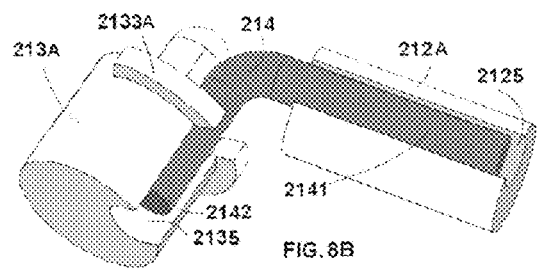
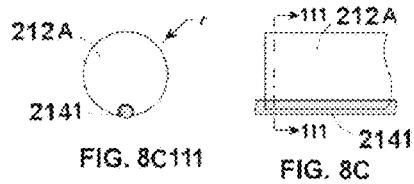
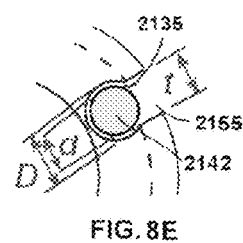
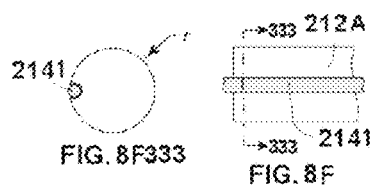
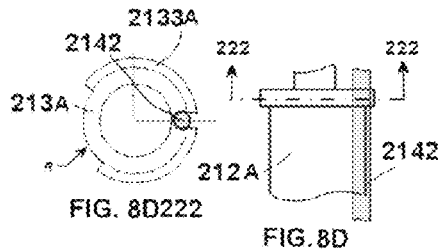
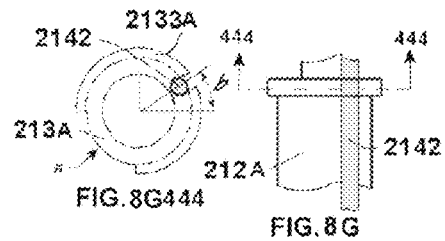

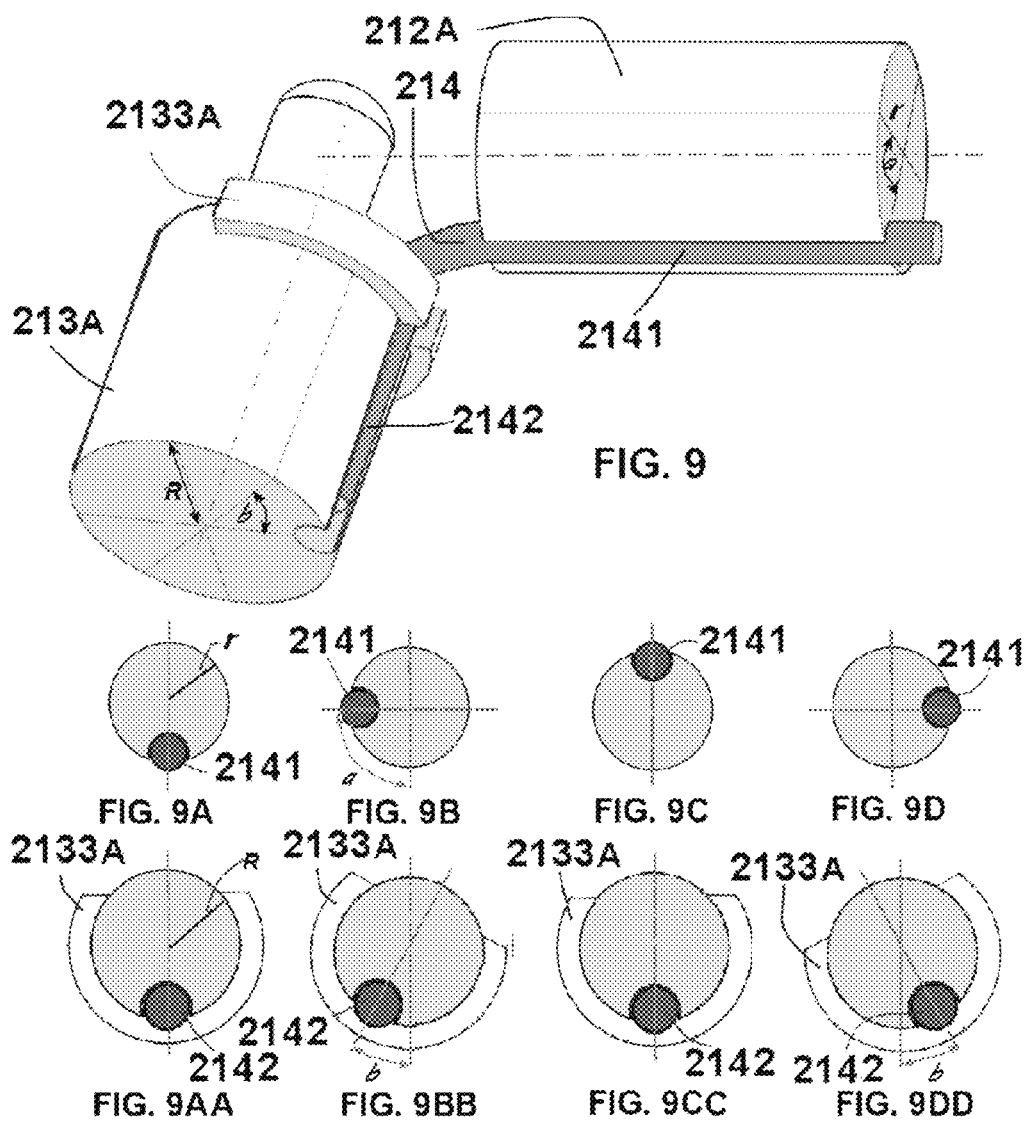

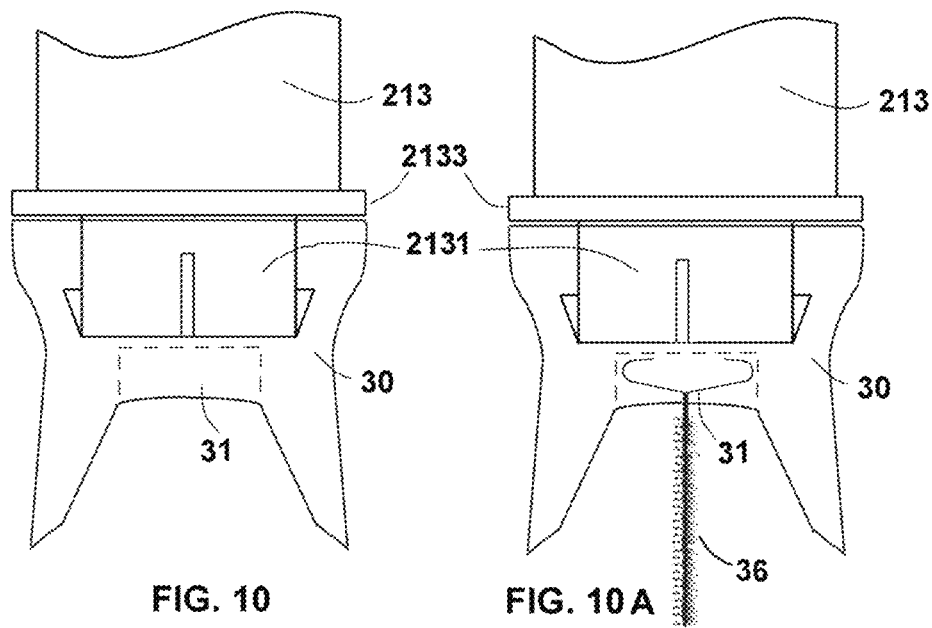

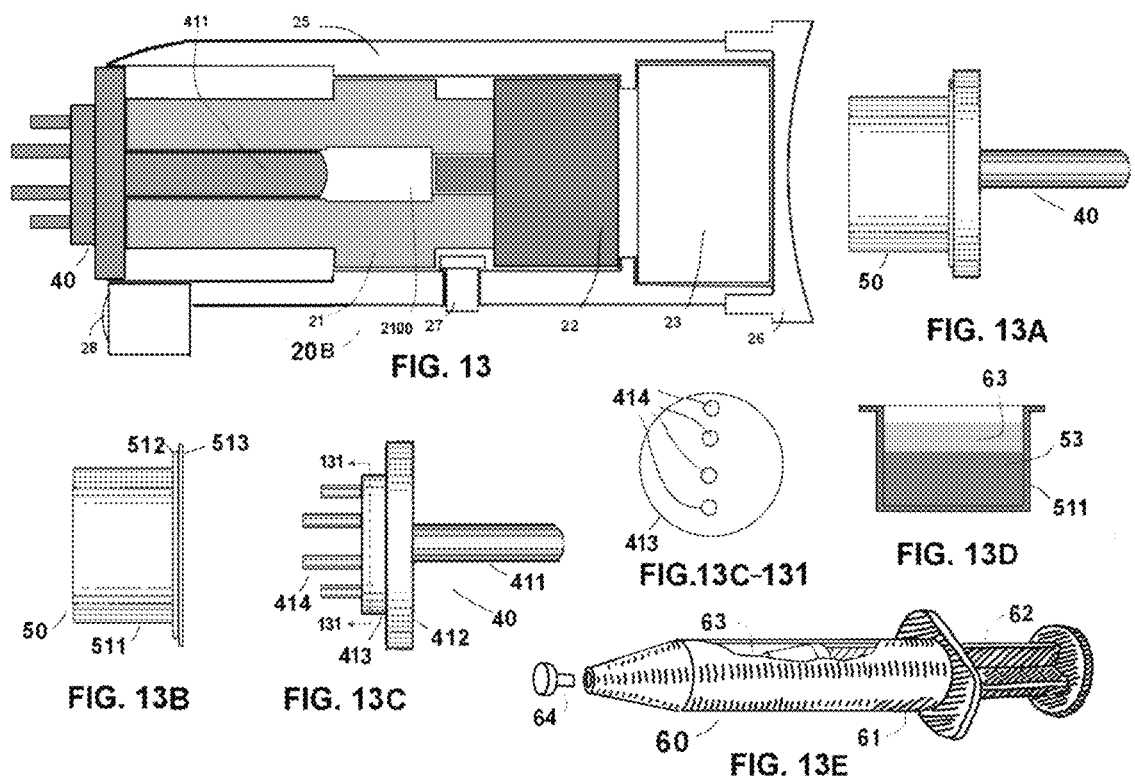

PORTABLE SIMULTANEOUS TOOTH POLISHING AND BLEACHING SYSTEM USING A FULL-CONTACT SWINGING MECHANISM

CROSS-REFERENCE TO RELATED APPLICATIONS

| U.S. Patent Documents | | | |
|---|---|---|---|
| Patent Number | Published Date | Inventors | Current U.S. Class |
| 10,092,382 | Oct. 9, 2018 | Wang et all | A61C 17/32; A61C/1/12 |
| 9,839,599 | Dec. 12, 2017 | Reierson et al | 524/453; 424/53 |
| 9,782,338 | Oct. 10, 2017 | Chen | 424/53; 424/49; 424/401 |
| 9,636,198 | Aug. 18, 2016 | Kodama | 433/32; 433/224; 433/25; 433/18 |
| 9,398,938 | Jul. 26, 2016 | Rek | 433/125; 433/118; 433/126; 433/127 |
| 8,814,566 | Aug. 26, 2014 | Carron at al | 433/103; 433/112; 433/114; 433/115 |
| 8,574,555 | Nov. 5, 2013 | Longo et al | 424/53; 424/49; 424/78.25 |
| 8,353,700 | Jan. 15, 2013 | Michaelian | 433/112; 433/114; 433/125; 433/133 |
| 8,303,939 | Nov. 6, 2012 | Speronello et al | 424/53; 424/613; 424/661 |
| 8,226,932 | Jul. 24, 2012 | Haught et al | 424/49 |
| 7,762,813 | Jul. 27, 2010 | Seals et al | 433/124; 433/125 |
| 7,601,002 | Oct. 13, 2009 | Milanovich et al | 433/215 |
| 7,530,808 | May 12, 2009 | Cao et al | 433/89; 222/145.5 |
| 7,331,784 | Feb. 19, 2008 | Suzuki | 433/29; 433/37 |
| 7,255,559 | Aug. 14, 2007 | Shen et al | 433/125; 433/118; 433/166 |
| 7,160,111 | Jan. 9, 2007 | Baughman | 433/216; 433/140; 433/29; 600/242 |
| 7,156,659 | Jan. 2, 2007 | Pernot | 433/144; 433/133 |
| 7,153,133 | Dec. 26, 2006 | Chia et al | 433/125 |
| 7,094,393 | Aug. 22, 2006 | Montgomery | 424/53; 424/54; 424/55; 424/57 |
| 7,060,256 | Jun. 13, 2006 | Pellico | 424/53; 206/571; 424/401; 433/215 |
| 6,964,076 | Nov. 15, 2005 | Zhuan | 15/22.2; 15/22.1; 433/118; 433/122 |
| 6,908,607 | Jun. 21, 2005 | Banerjee et al | 424/53; 433/89; 433/97; 433/114 |
| 6,916,176 | Jul. 12, 2005 | Schatz et al | 433/126; 403/320 |
| 6,555,020 | Apr. 29, 2003 | Chadwick et al | 252/186.26; 424/53; 433/215 |
| 6,536,628 | Mar. 25, 2003 | Montgomery | 222/137; 424/53; 206/219; 206/221 |
| 6,511,319 | Feb. 28, 2003 | Hunter | 433/122; 433/125 |
| 6,294,155 | Sep. 25, 2001 | Thomas et al | 424/49; 423/339 |
| 6,280,707 | Aug. 28, 2001 | Peterson et al | 424/49; 514/731; 514/734; 514/736 |
| 6,247,931 | Jun. 19, 2001 | Postal et al | 433/118; 433/122; 433/125 |
| 6,174,516 | Jan. 16, 2001 | Curtis et al | 424/53; 424/613; 424/616 |
| 6,168,433 | Jan. 2, 2001 | Hamlin | 433/125 |
| 5,931,672 | Aug. 3, 1999 | Postal et el | 74/54; 74/569; 433/122; 433/125 |
| 5,928,628 | Jul. 27, 1999 | Pellico | 424/49; 424/53 |
| 5,902,107 | May 11, 1999 | Lowell | 433/130; 433/112; 433/125 |
| 5,858,332 | Jan. 12, 1999 | Jensen | 424/53; 433/216; 252/186.25 |
| 5,822,821 | Oct. 20, 1998 | Sham | 15/22.1; 15/23 |
| 5,749,728 | May 12, 1998 | Bailey | 433/125; 433/126 |
| 5,766,574 | Jun. 16, 1998 | Christina-Beck et al | 424/53; 424/49; 424/613; 424/616 |
| 5,571,012 | Nov. 5, 1996 | Witherby et al | 433/125; 433/126; 433/133 |
| 5,531,599 | Jul. 1, 1996 | Bailey | 433/125; 433/126; 464/181 |
| 5,503,555 | Apr. 2, 1996 | Bailey | 433/126; 433/125 |
| 5,433,605 | Jul. 18, 1995 | Strobl | 433/112; 433/125; 433/126; 433/130 |
| 5,423,679 | Jun. 13, 1995 | Bailey | 433/125; 433/126 |
| 5,374,189 | Dec. 20, 1994 | Mendoza | 433/125; 433/132 |
| 5,328,369 | Jul. 12, 1994 | Bailey | 433/125; 433/126 |
| 5,171,564 | Dec. 15, 1992 | Nathoo et al | 424/53; 424/613; 424/614; 424/615 |
| 5,139,421 | Aug. 18, 1992 | Verderber | 433/31; 433/30 |
| 5,074,788 | Dec. 24, 1991 | Nakanishi | 433/115; 433/129 |
| 4,849,213 | Jul. 18, 1989 | Schaeffer | 424/53; 424/616 |
| 4,681,540 | Jul. 21, 1987 | Landgraf et al | 433/126; 422/131; 422/29; 433/131 |
| 4,648,838 | Mar. 10, 1987 | Schlachter | 433/29; 433/126; 433/80 |
| 4,460,341 | Jul. 17, 1984 | Nakanishi | 433/122; 433/125 |
| 4,460,337 | Jul. 17, 1984 | Landgraf et al | 433/29 |
| 4,401,616 | Aug. 30, 1983 | Wagner | 264/138; 264/16; 264/219; 264/322 |
| 4,382,790 | May 10, 1983 | Loge et al | 433/126 |
| 4,371,341 | Feb. 1, 1983 | Nakanishi | 433/118; 433/122; 433/127; 433/124 |
| 4,341,519 | Jul. 27, 1982 | Kuhn et al | 433/122; 433/121 |
| 3,967,380 | Jul. 6, 1976 | Malata | 32/27; 32/57; v279/l |
| 2017/0202652 | Jul. 20, 2017 | Wang et el | A61C 17/32; A61C/1/12 |
| 2015/0272712 | Oct., 1, 2015 | Shah | A61C 17/005; A61C 1/12 |
| 2012/0258418 | Oct. 11, 2012 | Shen | 433/29; 433/122; 433/82 |
| 2010/0035205 | Feb. 11, 2010 | Wang et al | 433/133 |
| 2006/0127844 | Jun. 15, 2006 | Michaelian | 433/125; 433/84 |
| 2005/0050658 | Mar. 10, 2005 | Chan et al | 15/22.1; 433/29 |

-continued

| U.S. Patent Documents | | | |
|---|---|---|---|
| 2003/0180688 | Sep. 25, 2003 | Vocaturo et al | 433/215; 433/80 |
| 2001/0046477 | Nov. 29, 2001 | Wolfe | 424/53 |

| China Patent Document | | | |
|---|---|---|---|
| Patent Number | Applied Date | Inventors | Current China Class |
| 201110154615.6 | 2011 Jun. 10 | Shen | A61C17/16 (2006.01) I |

BACKGROUND OF THE INVENTION

(1) Field of the Invention

The present invention relates to dental polishing and bleaching at home and at a dental clinic. The invention includes a bleaching handpiece with an electrically powered driver, a detachable swinging angle, a rubber cup, a dual-agent mixing set, and a user-specific-formed gum cover consisting of thermoplastic material to avoid the possible irritation from the bleaching agent. The swinging angle's input axis and the output axis forms an obtuse angle. The invention polishes and at the same time bleaches tooth surfaces.

Splatter of agents from the action of the rubber cup causes discomfort in the mouth and reduced effectiveness. The quick loss of agents in the cup from the splatter further causes process delay because time is spent on repeated manual replenishing of agent to the cup. The present invention transfers a continuous rotational input into a back-and-forth swinging output through a full-contact swinging mechanism to reduce agents' splatter.

For longer bleaching shelf life and more effective bleaching action, the present invention includes a dual agent mixing set that mixes a low pH bleaching agent, which is dominated by hydrogen peroxide, with a high pH polishing agent, which is dominated by pelelith powder, at the time of use. By applying the mixed dual-agent paste on tooth surfaces, the swinging movement of the rubber cup polishes and bleaches the tooth surface simultaneously.

For soft tissue protection, the user-specific-formed thermoplastic gum cover holds the mouth open at an optimal pose and covers the gingiva and lips. It achieves tooth surface bleaching with no irritation. During operation the heat from the movement of the rubber cup, plus the heat produced from the LED light on the bleaching handpiece which is directed to user's teeth improves the effectiveness of bleaching.

(2) Description of Related Art

Conventionally, tooth polishing and tooth bleaching are done as two separate procedures in dental treatment. This sequential polishing and bleaching are time-consuming; a method of combining the two procedures simultaneously is desirable. Hence the background analysis can be separated into two sections: a mechanical polishing design and a chemical bleaching design.

A. Mechanical Polishing Design

A conventional prophylaxis dental piece such as a prophylaxis angle is used to remove plaque and to polish the dentin surface of a tooth. A prophy cup is secured to the prophylaxis angle and is rotated by a driving torque from a dental tool, such as a low-speed dental driver. A typical drive mechanism is a gear connection between a driving rotor gear and a driven rotor gear at a right angle. The continuous rotation is thereby transferred from the driving dental tool to the same continuous rotation of the prophy cup at a right angle.

This gear connection as a prophylaxis method has several drawbacks. First, the gear structure of the disposable driving or driven rotors is costly to manufacture. Secondly, the small plastic gears are quickly worn out, so it is not suitable for long-period operation such as bleaching purposes. Thirdly, the gear contact produces heat with large operating noise and vibration. Fourthly, the gear connection between rotors usually only transfers continuous rotation which splatters the paste excessively during operation. Fifthly, the gearing engagement between driving and driven rotors is not suitable for an obtuse angle connection which makes the user feel more comfortable because it allows the user to maintain a neutral wrist position.

Products with non-gear connection or obtuse connection have been on the market; however, their complicated designs cause large size and high cost.

Previous patents describe improvements in the gear mechanism or non-gear methods to achieve operation at a right angle or at angles larger than 90 degrees, such as U.S. Pat. 2010/0035205, 2009/0035719, 2006/0127844, 2005/0214712, U.S. Pat. Nos. 9,017,073, 8,814,566, 8,353,700, 7,762,813, 7,255,559, 6,916,176, 6,247,931, 6,168,433, 5,902,107, 5,749,728, 5,571,012, 5,531,599, 5,503,555, 5,433,605, 5,423,679, 5,374,189, 5,328,369, 5,074,788, 4,681,540, 4,460,337 and 4,382,790. However, in the present market, the products from those patents exhibit cost and noise disadvantage.

U.S. Pat. No. 7,153,133 discloses a non-gear transmission assembly which uses multiple linkage shafts to connect a driving shaft and a head mount, both with multiple mounting holes. Each linkage shaft rotates and slides in the corresponding mounting holes in the driving shaft and the head mount. It overcomes the gear-transfer weakness; but the small mounting holes on the driving shaft and head mount make assembling time-consuming. The arm required to produce the required torque also limits the device size miniaturization. Furthermore, the multiple linkage rotational connection, which is similar to gear connection, can produce only a continuous rotational output.

U.S. Pat. No. 6,964,076 and 5,822,821 disclose a gear transmission assembly which converts rotational movement from the motor output member, through a straight cam slot, into a rotational reciprocating movement to achieve an oscillatory output with a small swing angle. However since the cam slot in those patents is straight, the time the cam slot swings to one direction is longer than the time the cam slot swings back to the other direction so that the output of the rotational reciprocating movement is not even. In other words, the reciprocation of the tooth brush will go faster in one direction than in the other direction. Moreover, the complicated gear-transfer mechanism in those patents limits the cam slot size for use in a compact dental handpiece space. Therefore, in a small design the driving torque will not be large enough for teeth polishing that uses high viscosity pastes.

U.S. Pat. No. 3,967,380, 4,341,519, 4,371,341 and 4,460,341 disclose the non-gear right-angle reciprocating transmission by a connection of a guide rolling rod, which is eccentrically located on the end of a rotatable driving shaft, and a longitudinal guide bore on the cylindrical surface of a reciprocable driven rotor. The contact inter-engaging surface of the driven rotor could be straight or concave cylindrical. The rotatable driving shaft provides a radial torque of the return stroke to the longitudinal bore which accepts a loose and slidable insertion of the rolling rod, coupling the continuous rotation of the driving shaft to the reciprocating swing of the driven rotor to achieve an oscillating output. U.S. Pat. No. 6,511,319 in 2003 applied the reciprocating transmission to a shaft with a pin at its flat end, which extends from a location offset from the central longitudinal axis of the shaft, to accept the dental handpiece driver and to permit the pin to engage in a grooved slot in a manner such that the shaft rotates and imparts an oscillating arcuate motion to the rotor. In this design, the contact length of the pin on the shaft with the groove on the rotor is only partial and varying during a shaft rotation cycle.

Based on the above non-gear right-angle reciprocating transmission by rolling rod and longitudinal bore, U.S. Pat. No. 6,247,931 and 5,931,672 developed a similar but different non-gear right-angle transmission by using an inter-engaging cam connection instead of the rod-bore connection. The camming surfaces are shaped with alternating hills and valleys to ensure a continuous contact during operation; however the complicated cam curve shape results in production cost weakness plus a large repulsive backward force. Also with that cam connection, similar to the gear connections, it is hard to achieve an obtuse connection between the driving and driven rotors. Furthermore, based on the camming surfaces in U.S. Pat. No. 6,247,931 and 5,931,672, U.S. Pat. No. 10,092,382 developed an altered inter-engaging conical surface cam structure to achieve an oscillation angle greater than 90 degrees, with a non-orthogonal output. However, the complicated cam curve shape still results in high production cost.

U.S. Pat. No. 9,398,938 discloses a non-gear transmission assembly which uses a longitudinal cavity suitable for coaxially containing a driving shaft, and a transversal cavity, arranged with an axis incident with the axis of the longitudinal cavity, to transform a rotary movement of a driving shaft into oscillating movement of a driven holder. The complicated cam-transfer mechanism and the small driving shaft diameter limit the size of the driven holder so that the driving torque will not be large enough against high-viscosity pastes.

U.S. Pat. 2012/0258418 removes the complicate gear connection and solves the uneven reciprocation problem in U.S. Pat. Nos. 6,964,076 and 5,822,821, but the curved cam slot still faces the manufacturing cost and size limitation.

B. Chemical Bleaching Design

Color changing of teeth results from either extrinsic or intrinsic staining. Extrinsic staining can be removed by mechanical method of tooth surface cleaning such as polishing treatment. Intrinsic staining occurs when staining compounds penetrate the enamel and even the dentin.

One conventional tooth intrinsic bleaching method is to place peroxide, either hydrogen peroxide or carbamide peroxide, upon a patient's teeth, such as described by U.S. Pat. No. 5,171,564. The oxidation-reduction reaction of peroxide bleaches the enamel of the teeth. However, hydrogen peroxide is a liquid that is difficult to stay on teeth surfaces, and moreover the high percentage hydrogen peroxide is harmful to teeth gingiva and mucosa of the mouth. Carbamide is a gel compound that contains hydrogen peroxide at a ratio of 1:3, which is usually placed in a dental tray, applying to the patient's teeth for a length of time ranging from hours to overnight. While the aqueous hydrogen peroxide breaks down and releases most of its bleaching power within 30-60 minutes, the gel carbamide peroxide slowly releases about 50% of its whitening power in the first two hours.

The hydrogen peroxide on the patient's teeth is not effective if the enamel rods of the teeth are closed. One method of facilitating the opening the enamel rods during bleaching is acid etching. When an acid of sufficient concentration is applied to the teeth, the chemical action of the acid serves to open the enamel rods of the teeth. However, this method is potentially harmful to the gingiva and is also time consuming. Another method involves the use of a pre-mixed carbamide and dental abrasive agent mixture to apply to the teeth and is then burnished onto the teeth. The dental abrasive agent in the prophy paste serves to abrade the tooth surfaces, accomplishing three objectives: (a) opening the enamel rods to facilitate their uptake of the peroxide; (b) removing stains from the tooth enamel through a mechanical scrubbing action; and (c) polishing the tooth enamel through a mechanical buffing action. To decrease tooth sensitivity during bleaching, fluoride can be included in the dental abrasive agent. However, a disadvantage of this method is that it delivers weakened carbamide to the teeth, resulting in less effective whitening. In addition, most readily and economically available carbamides are unstable, losing much of their oxygen (thus being reduced) when exposed to air and when mixed with other ingredients such as prophy paste for an extended period. Therefore, the effectiveness of pre-mixed peroxide as a tooth whitener is limited.

To overcome these drawbacks, previous patents have been published. Those patents either use pre-mixed compounds such as U.S. Pat. 2005/0050658, U.S. Pat Nos. 7,601,002, 6,555,020, 6,294,155, 6,174,516, 5,928,628, and 5,858,332, or provide an instant mixing method during usage such as U.S. Pat. 2001/0046477, U.S. Pat. Nos. 9,782,338, 7,530,808, 6,908,607, 6,681,957, 6,536,628, 6,176,396 and 5,766,574, which use a dispenser for mixing the prophy paste with the bleaching agent. U.S. Pat. 2008/0311057 provides an instant mixing method during usage, but only suitable for low-viscosity bleaching purpose without high-viscosity polishing function. U.S. Pat. Nos. 7,331,784 and 9, 636,198 use light irradiation or heat generator to warm up tooth surfaces for accelerating whitening process, but they are complicated with high manufacturing cost. U.S. Pat. No. 7,094,393 maintains the bleaching compounds with a pH range of 6.0 to 10.0 in presence of a calcium chelating agent to achieve the bleaching time of less than one hour. U.S. Pat. No. 7,060,256 uses two-component gel of increased peroxide content, but needs a dental bleaching tray to apply on the teeth. U.S. Pat. No. 4,401,616 uses a thermoplastic sheet material to make custom dental impression trays for individual users.

BRIEF SUMMARY OF THE INVENTION

There are ten major aspects of this invention that address the drawbacks of the current technology.

The first aspect of the invention is a bleaching handpiece-swinging angle combination that uses a non-gear, full-contact swinging mechanism to convert a continuous rotation of driving shaft to a back-and-forth swinging output of a driven rotor. The driven rotor then connects to a disposable rubber cup filled with the mixed polishing and bleaching agents to apply to the tooth surface. By comparison with the continuous rotation, the back-and-forth swinging output reduces agent paste splatter during operation. The splatter reduction and consequently slow loss of agent eliminate the discomfort in the mouth and renders the operating more efficient because the practitioner saves time that are otherwise spent on replenishing agent to the rubber cup. In addition, the non-gear transferring mechanism ensures a longer operation life compared to the geared mechanisms.

The second aspect of the invention is that in the swinging angle, the axes of the driving shaft and the driven rotor are engaged an obtuse angle so that the operation can be done more ergonomically by having a neutral wrist holding position.

The third aspect of the invention is that, in the full-contact mechanism, a protruding tilted off-axis rod at the output end of the driving shaft pushes inside a receiving vertical side slot in the driven rotor to transfer the continuous rotation of the driving shaft to the back-and-forth swinging of the driven rotor. This is achieved by the receiving vertical side slot being parallel to the axis of the driven rotor, and the concave shape of the driving shaft output end matching the domed shape of the driven rotor. Because of the shape matching, the full length of the tilted off-axis rod of the driving shaft make contact with the receiving vertical-slot the driving rotor all the time during operation. This full contact at all times results a much longer operating life than the geared connections that are common in the present prophy angle market.

The fourth aspect of the invention is that the driving shaft is axially positioned by a toothed retainer, such as an externally toothed lock washer, to restrict the driving shaft axially from backing out during operation. During assembling, the toothed retainer is pressed into the angle casing. Because the out diameter of the retainer is slightly greater than the inner diameter of the angle casing, during operation the teeth of the retainer bite into the inner wall of the angle casing.

The fifth aspect of the invention is that, in the instance of bent-rod-driving mechanism, a bent driving rod connects the bent-rod-driving shaft to the bent-rod-driven rotor, to transfer the continuous rotation of the driving shaft to the back-and-forth swinging of the bent-rod-driven rotor. The bent driving rod has the same obtuse angle as the angle between the driving shaft and the driven rotor. This transfer mechanism is designed with the radius of the bent-rod-driven rotor being bigger than the radius of the bent-rod-driving shaft, and with the swing angle equal to arcsine of the ratio of the radius of the bent-rod-driving shaft to the radius of the bent-rod-driven rotor.

The fifth aspect of the invention a mortise-and-tenon joint that connects the rubber cup to the driven rotor. The driven rotor output end is the square tenon; the rubber up input end is the rectangular mortise to match the tenon when assembled. The deformation of the rubber creates a force to allow a tight fit. The square tenon has a vertical slit at the center of the output end of the driven rotor, making it slightly thinner when squeezed for easy assembling.

The sixth aspect of the invention is that the swinging of the driven rotor has a momentary pause when the swinging direction changes. It is achieved by having the width of the driven slot slightly bigger than the diameter of the driving rod. This design reduces the impulse on the driven rotor, as well as vibration.

The seventh aspect of the invention is that the transferring of the continuous rotation to the back-and-forth swinging movement operates identically regardless of the clockwise or counterclockwise rotational direction of the driving shaft. This is due to the symmetrical structure of the receiving vertical side slot of the driven rotor.

The eighth aspect of the invention is a dual-agent mixing set that includes a dual-agent bowl with a polishing agent, and a bleaching agent individually pre-installed for long-term storage. By applying the mixing adaptor powered by the bleaching handpiece just before usage, the bleaching agent is mixed with the polishing agent. The bleaching agent is dominated by the hydrogen peroxide with low pH stabilizers whereas the polishing agent is dominated by pelelith powder with high pH accelerators. With the proper volumetric proportion of the two agents, the resultant pH value of the mixed agents is optimal for bleaching efficiency.

The ninth aspect of the invention is a pre-shaped thermoplastic gum cover that fits the profile of the individual user's teeth and mouth to cover the gingiva and lips and also to keep the mouth open properly. It protects the user's soft tissue from contacting the bleaching agent during operation. The material is polycaprolactone (PCL). The cover is user specific as the specificity is formed by a reshaping process in hot water.

The tenth aspect of the invention is that the components of the swinging angle with the rubber cup in the bleaching system is usable alone as a prophylaxis angle to mate to a standard powered driver at a dental clinic. The swinging angle provides the back-and-forth swinging movement on teeth surfaces by the full-contact swinging mechanism.

BRIEF DESCRIPTION OF THE SEVERAL VIEWS OF THE DRAWING

The invention will be further described in conjunction with the attached drawings:

FIG. 3A shows the longitudinal cross-sectional view of the bleaching handpiece with the swinging angle attached, while

FIG. 4 displays the details of the swinging angle in FIG. 3A. FIG. 4-1 is its side view from the input end i.e., from the right hand side of the swinging angle, showing a toothed retainer, such as an externally toothed metal lock washer, being locked in the angle casing. FIG. 4A is the driven rotor assembled with the driving shaft in place, while FIG. 4AA views the same driven rotor after the driving shaft is rotated 90 degrees. FIG. 4B is the output section of the driving shaft while FIG. 4BB is after the 90 degrees rotation.

FIG. 5A through FIG. 5BD illustrate the relationship between the driving shaft and the driven rotor during operation when the driving shaft rotates clockwise, i.e. right-handed turn. FIG. 5A and FIG. 5B show two representative positions of the driving shaft with the tilted off-axis rod and the driven rotor before and after a 90 degrees rotation. FIG. 5AC and FIG. 5BC are the right end views while FIG. 5AD and FIG. 5BD are respectively top views.

FIG. 6 illustrates the details of the interaction between the output end of the driving shaft and the driven rotor during operation. FIG. 6-1 and FIG. 6-2 show the top view of a quarter-turn positions of the driving shaft in relation to the driven rotor. FIG. 6A, FIG. 6B, FIG. 6C and FIG. 6D show the four positions of the tilted off-axis rod rotated clockwise every 90 degrees starting from the top position, while FIG. 6AA, FIG. 6BB, FIG. 6CC and FIG. 6DD are the corresponding positions of the driven rotor.

FIG. 7 illustrates the alternative bent-rod swinging angle shown in FIG. 3B. FIG. 7A shows the connection of the bent-rod-driving shaft to the bent-rod-driven rotor driven by the bent driving rod. FIG. 7A1111 and FIG. 7A2222 are the cross-sectional view from cutting plane in the bend-rod-driving shaft and the bent-rod-driven rotor, respectively, in FIG. 7A.

FIG. 8A through FIG. 8G444 illustrate the relationship of the bent-rod-driving shaft and the bent-rod-driven rotor during operation when the bent-rod-driving shaft rotates 90 degrees clockwise. FIG. 8A and FIG. 8B are isometric views of the three moving elements in the two representative positions. FIG. 8C with its cross-sectional view FIG. 8C111, and FIG. 8D with its cross-sectional view FIG. 8D222, are cross-sectional views of the bent-rod-driving shaft and the bent-rod-driven rotor in FIG. 8A. FIG. 8F, FIG. 8F333, FIG. 8G and FIG. 8G444 are the corresponding cross-sectional views of FIG. 8B. FIG. 8E is an enlarged cross-sectional view of the bent driving rod inside the mounting slot of the driven rotor, showing the approximate dimensional relationships of the bent driving rod, the mounting slot, and the slot opening.

FIG. 9 series of figures show the rotational positions of a complete cycle during operation of the bent-rod-driving shaft and the bent-rod-driven rotor with the bent driving rod FIG. 9 is an isometric view of the bent-rod-driving shaft and the bent-rod-driven rotor with the bent driving rod. FIG. 9A, FIG. 9B, FIG. 9C and FIG. 9D show the rotation of the bent-rod-driving shaft at every 90 degrees counterclockwise to complete a cycle. FIG. 9AA, FIG. 9BB, FIG. 9CC and FIG. 9DD are the corresponding positions of the bent-rod-driven rotor.

FIG. 10 is the output end of the driven rotor with the rubber cup connected by a mortise-and-tenon joint. FIG. 10A shows a detachable interdental brush inserted in the rubber cup.

FIG. 11 displays the details of the output end of the driven rotor, while FIG. 11-555 is the transverse cross-sectional view of the square tenon at the bottom end.

FIG. 12 is a cross-sectional view of the rubber cup shown in FIG. 10, while FIG. 12-666 is another cross-sectional side view orthogonal to FIG. 12. The top opening of the rubber cup matches the bottom end of the driven rotor (refer to FIG. 10). The frustoconical shaped bottom opening accepts the dual-agent paste. Moreover a split cut is located centrally at the bottom end of the rubber cup for accepting the interdental brush.

FIG. 13 shows the same handpiece in FIG. 3A except the swinging angle is replaced by the mixing adaptor of the dual-agent mixing set (refer to FIG. 1). FIG. 13A is an isometric view after the mixing adaptor is inserted in the dual-agent bowl while FIG. 13B is the view of the dual-agent bowl alone. FIG. 13C is an isometric view of the mixing adaptor, while FIG. 131 is a transverse cross-sectional view in FIG. 13C. FIG. 13D is the dual-agent bowl showing the bleaching agent added on the top of the pre-installed polishing agent. FIG. 13E shows the syringe with the bleaching agent pre-installed.

FIG. 15A777 is the cross-sectional view of the gum cover.

DETAILED DESCRIPTION OF THE INVENTION

Figure 1:
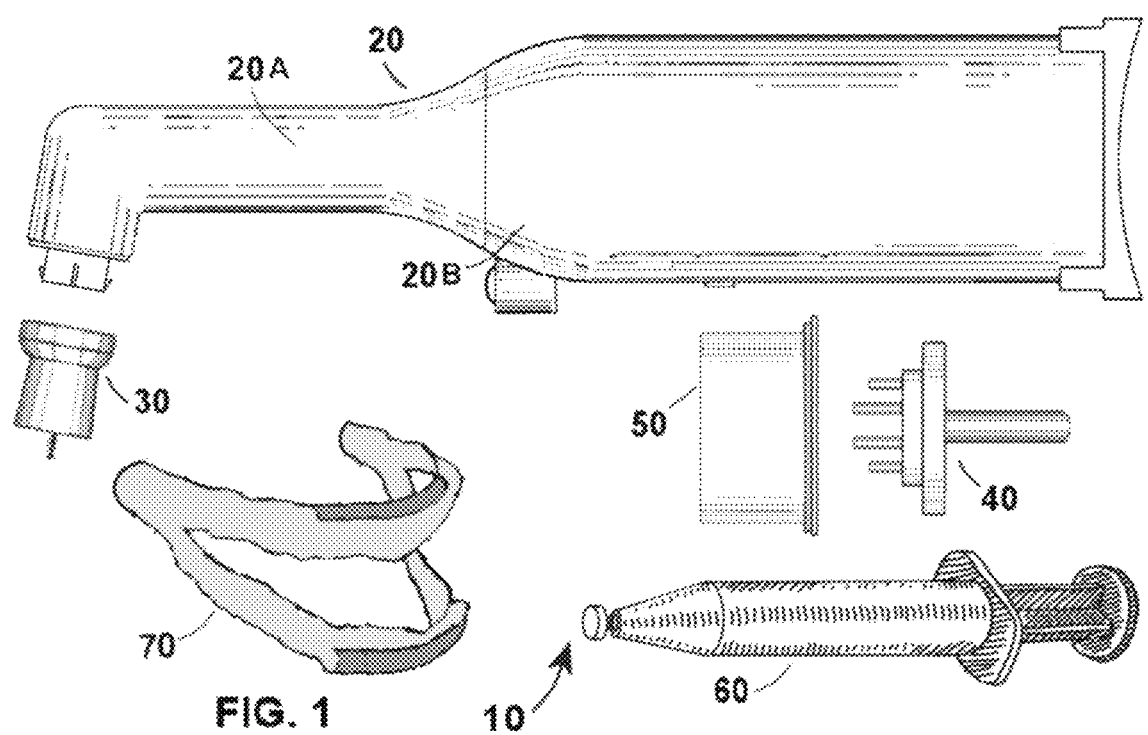
FIG. 1 shows the tooth polishing and bleaching system that has three subdivisions: 1) a bleaching handpiece with an electrically powered driver and user control, and a detachable swinging angle with a disposable cup attached, 2) a dual-agent mixing set which consists of a mixing adaptor, a disposable dual-agent bowl, and a bleaching agent syringe, and 3) a user-specific-formed thermoplastic gum cover with centrally protruding flanges.

FIG. 1 shows three subdivisions of the tooth polishing and bleaching device 10: 1) a bleaching handpiece swinging angle subassembly 20 and a disposable-rubber cup 30, 2) a dual-agent mixing set which consists of a mixing adaptor 40, a disposable polishing agent bowl 50 and a disposable bleaching agent syringe 60, and 3) a user-specific-formed thermoplastic gum cover 70 which consists of an upper and lower protection arch with centrally protruding flanges. The bleaching handpiece swinging angle subassembly 20 is inserted into an electrically powered driver set 20B. The rubber cup 30 is to be attached at the output end of the swinging angle 20A.

Figure 2:
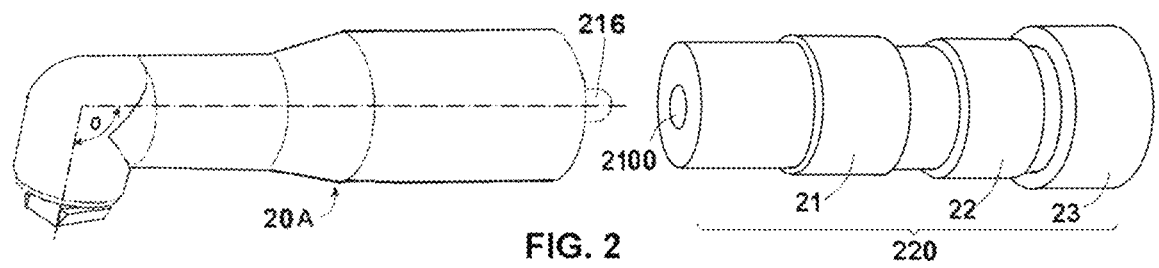
FIG. 2 is view of the major elements of the handpiece and the swinging angle in FIG. 1 before assembling: a swinging angle that has an obtuse angle and a driving supply group in the electrically powered driver to provide the rotational input to the swinging angle.

FIG. 2 is an isometric view of the swinging angle 20A, which has an obtuse angle O between its input shaft and the output end, and an isometric view of the supply group 220 of the electrically powered driver set 20B. The supply group 220 includes a direct current (DC) electric motor 22 with a continuous rotation output, a battery 23 for providing DC power to the electric motor 22, and a matching adaptor 21 that connects the output end of the DC electric motor 22 and couples via the central chuck 2100 to the shaft tail 216 at the input end of the swinging angle 20A. The swinging angle 20A employs the full-contact swinging mechanism to transfer a continuous rotation into a back-and forth swinging motion.

Figure 3A:
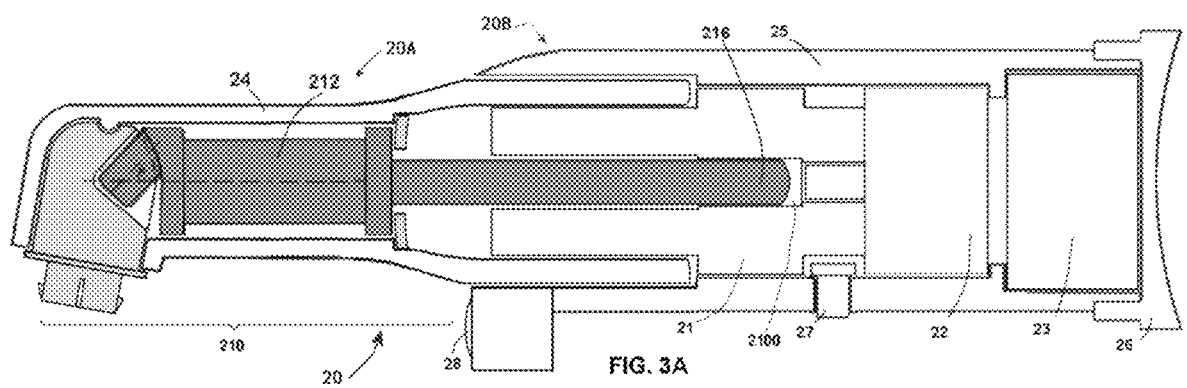

FIG. 3A is a longitudinal cross-sectional view of the bleaching handpiece swinging angle subassembly 20 where the swinging angle 20A (refer to FIG. 1) is the instance of the full-contact swinging mechanism as shown in the tilted off-axis rod swinging angle 210. Here the moving elements inside are covered by the angle casing 24. The supply group 220 inside the handpiece housing 25 includes the matching adaptor 21, the DC electric motor 22 and the battery 23. A rear housing cap 26 attaches at the battery end of the handpiece housing 25 to position the battery 23 as well as to seal the handpiece housing 25. The shaft tail 216 at the input end of the tilted off-axis rod swinging angle 210 is inserted into the central chuck 2100 of the matching adaptor 21 to accept the rotational driving force. On the handpiece housing 25, there are a LED bulb 28 for providing illumination as well as heat, and a power switch 27 for controlling the on/off of the electric power.

Figure 3B:
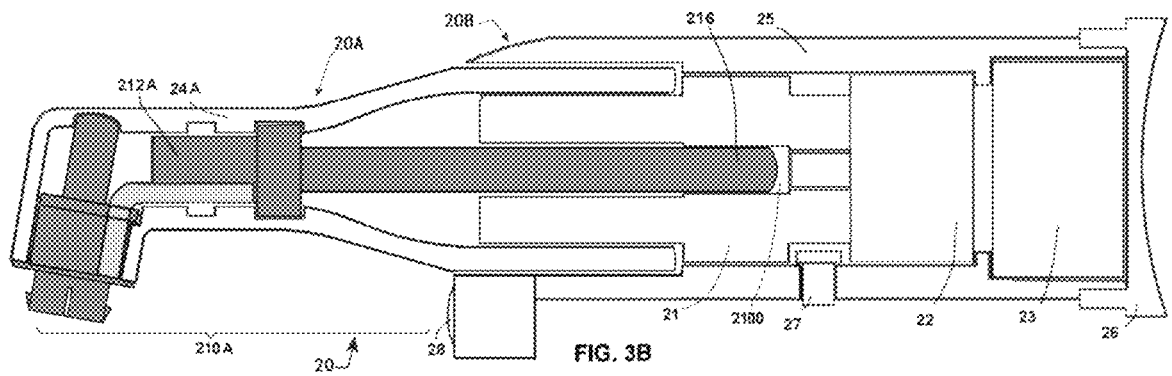
FIG 3B shows a bent-rod structure as an alternative to the tilted off-axis rod structure. The same electrically powered driver with user control is shown for the respective swinging angle in both alternatives.

FIG. 3B is the longitudinal cross-sectional view of the bleaching handpiece swinging angle subassembly 20 where the swinging angle 20A is the alternative instance of the full-contact swinging mechanism: the bent-rod-driving mechanism which employs the bent-rod swinging angle 210A, with different inside elements and a different bent-rod-driving angle casing 24A.

FIG. 4 illustrates the details of the moving elements in the tilted off-axis rod-swinging angle 210 shown in FIG. 3A. The rotational axis of the shaft 212 and the rotational axis of the driven rotor 213 form the same obtuse angle O in FIG. 2.

At the output end of the shaft 212 there is a tilted off-axis rod 217 on the concave-shaped front 2121. The tilted off-axis rod 217 forms an acute angle p with the axis of the driving shaft 212. The shaft tail 216 at the input end of the shaft 212 is inserted into the central chuck 2100 and accepts the rotational driving force from the matching adaptor 21 (refer to FIG. 3A).

FIG. 4 also shows that the driven rotor 213 has a domed trunk 2136 at its top end, and a square tenon 2131 at its bottom end. The domed trunk 2136 has a surface curvature that matches that of the curvature of the concave-sharped front 2121 of the driving shaft 212. An axial positioning flange 2133 is located at the mid-section of said driven rotor 213 above the square tenon 2131. At the bottom end of the square tenon 2131 there is a pair of external ridges 2132 that forms a barb. The square tenon 2131 of the driven rotor 213 inserts into the rubber cup 30 which features a rectangular mortise, which deforms when assembled to fit tightly on the tenon to form a mortise-and-tenon joint (Refer to FIG. 10).

FIG. 4-1 is the right end view of the tilted off-axis rod swinging angle 210, which shows the location of a toothed retainer 211 in relation to the inner wall of the casing 24 and the axial positioning of the driving shaft 212. At the mid-section of the shaft 212 there exists a positioning step 215. The toothed retainer 211 is inserted along the shaft tail 216 into the angle casing 24 until it touches the positioning step 242 on the inner wall of the angle casing 24. Since the diameter of the toothed retainer 211 is slightly greater than the inner diameter of the casing 24, multiple teeth 219 bend to the right-side to grab the inner wall of the casing 24. The toothed retainer 211 and the positioning shoulder 215 on the driving shaft 212 restrict the motion of the shaft 212 so that its only degree of freedom is rotation about its axis.

FIG. 4A is an isolated view of the rotor 213 and the tilted off-axis rod 217 of the driving shaft 212 in the subassembly. FIG. 4AA is the same isolated view after the driving shaft 212 is rotated 90 degrees. FIG. 4B and FIG. 4BB show the tilted off-axis rod 217 on the driving shaft 212 alone and correspond to FIG. 4A and FIG. 4AA, respectively. A fillet 2171 exists for durability.

When assembled, the tilted off-axis rod 217 of the driving shaft 212 moves inside the receiving vertical side slot 218 of the driven rotor 213 to transfer the continuous rotation of the driving shaft 212 into the back-and-forth swinging movement of the driven rotor 213. An alignment dimple 2137 at the top-center of the domed trunk 2136 matches the positioning protrusion 241 on the inner wall of the driving angle casing 24 to maintain axial position of the driven rotor 213. Together with the axial positioning flange 2133, the only allowed degree of freedom of the driven rotor 213 is rotation about its axis.

FIG. 5A and FIG. 5B show two representative positions of the driving shaft 212 and the driven rotor 213 during operation. These two positions differ by a 90-degree turn of the driving shaft 212. FIG. 5AC and FIG. 5BC are cross-sectional views of the driven rotor 213 with the tilted off-axis rod 217 in place at those two positions, respectively. Similarly, FIG. 5AD and FIG. 5BD are the respective top views.

As shown in FIG. 5AC, the width D of the receiving vertical side slot 218 is slightly bigger than the diameter d of the tilted off-axis rod 217, so that when the driven rotor 213 changes swinging direction, the tilted off-axis rod 217 needs time to travel across from touching one side of the receiving vertical side slot 218 to touching the other side. Therefore, a momentary pause takes place when the swinging changes direction. FIG. 5BD shows that the driven rotor 213 swings an angle b when the tilted off-axis rod 217 rotates 90 degrees.

FIG. 6, FIG. 6-1 and FIG. 6-2 show the motion of the output section of the tilted off-axis rod swinging angle 210. FIG. 6-1 and FIG. 6-2 are the top views of the tilted off-axis rod 217 and the concave-shaped front 2121 of the driving shaft 212 and the receiving vertical side slot 218 of the driven rotor 213. These two figures show the movement of a 90 degrees rotation of the driving shaft 212. This rotation results in a swing angle b.

FIG. 6A, FIG. 6B, FIG. 6C, and FIG. 6D are the axial views of the output end of the driving shaft 212 alone in four sequential rotational positions during operation. The concave-shaped front 2121 in the view is shown as a circle. The tilted off-axis rod 217 is shown with its rotational angle a, which would be 90 degrees if it rotated a quarter of revolution. The four sequential positions are when the driving shaft 212 rotates each quarter of a revolution clockwise in the view, causing the tilted off-axis rod 217 in the view to be in the four orientations as shown. For each quarter of a revolution, FIG. 6AA, FIG. 6BB, FIG. 6CC, and FIG. 6DD show the bottom-view of the driven rotor 213 at the four corresponding positions sequentially. When the driving shaft 212 rotates an angle a, the receiving vertical side slot 218 of the driven rotor 213 swings an angle b to one side, then continues by swinging back the same amount b to the opposite side.

FIG. 7 illustrates in detail how a bent-rod-driving shaft 212A drives a bent-rod-driven rotor 213A via a bent driving rod 214 in the bent-rod swinging angle 210A in FIG. 3B. The angle formed by axes of the bent-rod-driven rotor 213A and of the bent-rod-driving shaft 212A is the same obtuse angle O in FIG. 2. The bent driving rod 214 has a bent angle also equal to that obtuse angle.

The bent-rod-driving shaft 212A has a positioning collar 215A. It sits in the circular groove 244 next to the positioning step 243 in the bent-rod-driving angle casing 24A. The circular groove 244 constrains the shaft's movement to only one degree of freedom—rotation about its axis. The shaft tail 216 at the input end inserts into the central chuck 2100 (refer to FIG. 3B) and accepts the rotational driving force from the matching adaptor 21.

The bent-rod-driven rotor 213A has a positioning shaft 2134 that extends into a positioning dimple 241A on the inner wall of the bent-rod-driving angle casing 24A. The driven rotor 213A has a positioning flange 2133A at its mid-section that contacts a positioning step 245 on the inner wall of the bend of the bent-rod-driving angle casing 24A. Together with the axial positioning shaft 2134, the only allowed degree of freedom of the rotor is rotation about its axis.

The output end of the bent-rod-driven rotor 213A is the same as that of the driven rotor 213 which is described in FIG. 4. It uses the square tenon 2131 to inserts into the rubber cup 30 which features a rectangular mortise that deforms to match the square tenon using its elasticity, forming the mortise-and-tenon joint (refer to FIG. 10).

FIG. 7A shows the connection between the bent-rod-driving shaft 212A and the bent-rod-driven rotor 213A by the bent driving rod 214. With the bent driving rod 214 snapped on, the transverse cross-sectional view of cutting plane 1111-1111 on the bent-rod-driving shaft 212A is shown on FIG. 7A1111, while the view of cutting plane 2222-2222 on the bent-rod-driven rotor 213A is shown on FIG. 7A2222.

FIG. 8A is the isometric view of the subassembly that consists of the bent-rod-driving shaft 212A, the bent-rod-driven rotor 213A, and the bent driving rod 214 that is snapped in both the shaft 212A and the rotor 213A. FIG. 8B is a similar view of the subassembly but with the bent-rod-driving shaft 212A rotated 90 degrees, and the bent-rod-driven rotor 213A swung at angle b. The bent driving rod 214 is snapped into the axially co-linear driving shaft mounting slot 2125 of the shaft 212A at one end, and the axially co-linear driven rotor mounting slot 2135 of the rotor 213A at the other end. During operation, the straight rod-driving segment 2141 both rotates along the shaft 212A and slides inside the driving shaft mounting slot 2125; and the straight rod-driven segment 2142 both rotates along the rotor 213A and slides in the driven rotor mounting slot 2135.

FIG. 8C is the longitudinal cross-sectional view of the output end of the bent-rod-driving shaft 212A of the subassembly in FIG. 8A, while FIG. 8D is that of the bent-rod-driven rotor 213A. FIG. 8C111 is the transverse cross-sectional view from cutting plane 111-111 in FIG. 8C, while FIG. 8D222 is the transverse cross-sectional view from cutting plane 222-222 in FIG. 8D.

FIG. 8F and FIG. 8G continues the cross-sectional views with bent-rod-driving shaft 212A rotated 90 degrees clockwise as shown in FIG. 8B. FIG. 8F333 is the transverse cross-sectional view from cutting plane 333-333 in FIG. 8F, while FIG. 8G444 is the transverse cross-sectional view from cutting plane 444-444 in FIG. 8G, showing the swing angle b of the bent-rod-driven rotor 213A.

FIG. 8E is an enlarged view of the straight rod-driven segment 2142 of the bent driving rod 214 inside the driven rotor mounting slot 2135. It illustrates that the width t of the slot opening 2155 at top of the driven rotor mounting slot 2135 is slightly smaller than the diameter d of the bent driving rod 214, and that the arc diameter D of the driven rotor mounting slot 2135 is slightly bigger than the diameter d of the bent driving rod 214. Identically, the straight rod-driving segment 2141 of the bent driving rod 214 and the driving shaft mounting slot 2125 have the same width and dimensional relationship for applying the same snap-on mechanism.

Both the driving shaft mounting slot 2125 and the driven rotor mounting slot 2135 have the shape of a partial cylinder; therefore, each of their transverse cross-sectional views has a major arc with an arc measure of about 190°. The two straight segments of the bent driving rod 214 will rotate and slide freely inside the two mounting slots. Moreover the diameter of the bent driving rod 214 is slightly bigger than the depths of mounting slots 2125 and 2135. Therefore the bent driving rod 214 acts as a bearing mechanism between the bent-rod-driving shaft 212A (or the bent-rod-driven rotor 213A) and the inner surfaces of the bent-rod-driving angle housing 24A. Hence friction is reduced during operation.

FIG. 9 illustrates the mathematical relationship between the bent-rod-driving shaft 212A with radius r and the bent-rod-driven rotor 213A with radius R. For the bent-rod-driving shaft 212A to rotate an angle a, there is a corresponding swing angle b by the bent-rod-driven rotor 213A.

Because the radius r of the bent-rod-driving shaft 212A is smaller than the radius R of the bent-rod-driven rotor 213A, the bent-rod-driven rotor 213A always swings a smaller angle b than the angle α rotated by the bent-rod-driving shaft 212A. A revolution of the bent-rod-driven rotor 213A forces the bent-rod-driving shaft 212A to swing back and forth around its rotational axis. The swing angle b is related to the two radii by the equation: $\sin(b)=r/R$. Therefore, the swing angle b can be varied by the relation of r to R. In other words, the swing angle of the bent-rod-driven rotor 213A can be adjusted by the diametrical ratio of the bent-rod-driving shaft 212A over the bent-rod-driven rotor 213A.

FIG. 9A, FIG. 9B, FIG. 9C and FIG. 9D are the transverse cross-sectional view of the bent-rod-driving shaft 212A, together with the bent driving rod 214, in four sequential positions during operation, when the bent-rod-driving shaft 212A rotates each quarter of a revolution. The straight rod-driving segment 2141 of the driving rod 214 moves a rotational angle a clockwise in the view. Correspondingly, FIG. 9AA, FIG. 9BB, FIG. 9CC, and FIG. 9DD show the transverse cross-sectional view of the bent-rod-driven rotor 213A of the same four sequential positions that are driven by the rotation of the bent-rod-driving shaft 212A, with the straight rod-driven segment 2142 of the bent driving rod 214 shown. For a complete revolution of the bent-rod-driving shaft 212A, the bent-rod-driven rotor 213A swings an angle b to one side, then swings back the same amount b to the opposite side.

FIG. 10 is a longitudinal cross-sectional view of the bottom end of the driven rotor 213 (identical to the bent-rod-driven rotor 213A) with the rubber cup 30 assembled as a mortise-and-tenon joint. FIG. 10A shows the assembly with the detachable interdental brush 36 installed. At the middle bottom of the rubber cup 30 there is a split cut 31 to accept the inserting of an interdental brush 36. The rubber cup 30 is axially co-linear with the axis of the driven rotor 213 or 213A and fits tightly on the driven rotor, so that during operation the rubber cup 30 has the same swinging motion as the rotor 213 or 213A without slippage or detachment. The square tenon 2131 can be pressed onto and subsequently removed from the rectangular mortise 35 (refer to FIG. 12) at the top end of the rubber cup.

Figures 11, 555:
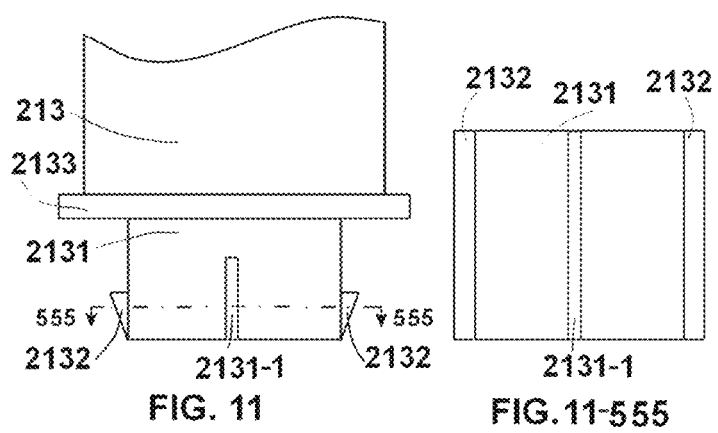

FIG. 11 shows the barb on the square tenon 2131 detailing a pair of external ridges 2132 at the bottom end. FIG. 11-555 is the transverse cross-sectional view of the square tenon 2131 from cutting plane 555-555 in FIG. 11, which also shows the external ridges 2132. At the center of the bottom end of the square tenon 2131, there is a slit 2131-1 parallel to the external ridges 2132. The slit 2131-1 allows the square tenon 2131 to deform inwards, hence reducing its thickness, when the square tenon 2131 is pressed into the rectangular mortise 35. After assembling, this rectangular shape is deformed to fit the square tenon tightly because of the rubber elasticity (refer to FIG. 12). The external ridges 2132 will act as barbs to prevent detachment of the rubber cup 30 during operation.

Figure 12:
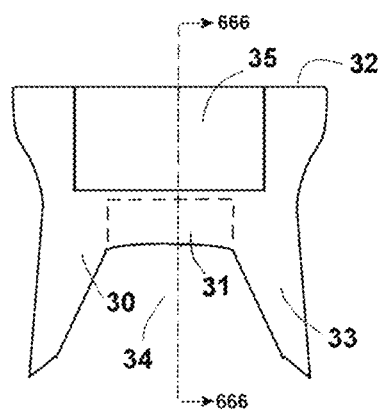
Figure 666:
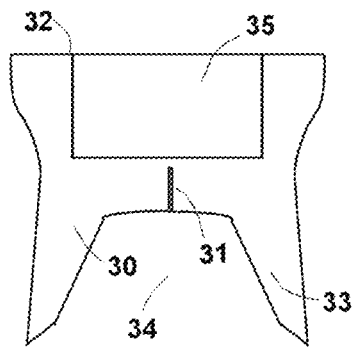

FIG. 12 shows the longitudinal cross-sectional view of the rubber cup 30. FIG. 12-666 is the cross-sectional view from cutting plane 666-666 in FIG. 12. The top end of the rubber cup 30 is a platform 32, which is abutted against the bottom of the axial positioning flange 2133 of the driven rotor 213 when assembled. The center of the platform 32 is the rectangular mortise 35. The rectangular mortise 35, which is of elastic rubber material, deforms to match the square tenon 2131 of the driven rotor 213 or 213A (refer to FIG. 11-555) when assembled. The split cut 31, bounded by dashed lines in the cup opening shown in FIG. 12, secures the interdental brush 36 (refer to FIG. 10A). A frustoconical shaped cup opening 33 at the bottom end forms a cup-bottom opening 34 for holding the dual-agent paste.

Figure 12A:
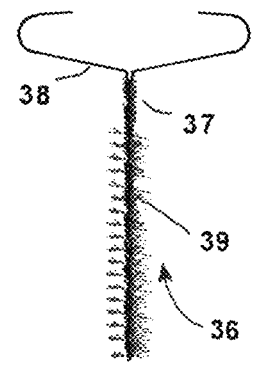
FIG. 12A shows the detachable interdental brush which is designed to insert into the bottom end of the rubber cup.

FIG. 12A illustrates the details of the interdental brush 36, which is to be inserted into the split cut 31 of the rubber cup 30 as shown in FIG. 10A. It comprises a twisted wire stem 37, a bifurcated wire handle 38 and a large quantity of brush fibers 39. Because of the elastic and high static friction properties of rubber, the interdental brush 36 is fastened in the cup after the wire handle 38 is inserted into the split cut 31. During operation, the brush fibers 39 work in the gaps between teeth with the back-and-forth swinging movement to clean and remove interproximal plaque.

FIG. 13 is a longitudinal cross-sectional view of the bleaching handpiece-swinging angle subassembly 20 in FIG. 3A and FIG. 3B, except the tilted off-axis rod-swinging angle 210 (or the alternative bent-rod swinging angle 210A) is replaced by a mixing adaptor 40. The mixing adaptor 40 contains a mixing shaft 411 at the input end (refer to FIG. 13 C) to insert into the central chuck 2100 of the matching adaptor 21 (refer to FIG. 2) to accept the continuous rotational driving force.

FIG. 13A is a side view of the mixing adaptor 40 that is inserted into the dual-agent bowl 50. FIG. 13B is a side view of the dual-agent bowl 50 with a high pH polishing agent pre-installed. The dual-agent bowl 50 consists of a bowl body 511 with a bowl flange 512, and a plastic cover sheet 513 to cover the bowl flange 512. FIG. 13C is a side view of the mixing adaptor 40. Its input end has an input-shaft 411 with a base disk 412 while its output end has blending pins 414 with a pin-base 413. The pin-base 413 matches the bowl body 511 of the dual-agent bowl 50 (refer to FIG. 13A). FIG. 13C-131 is a transverse cross-sectional view from cutting plane 131-131 shown in FIG. 13C, where the multiple blending pins 414 are aligned along the diameter of the pin-base 413. FIG. 13D is a longitudinal cross-sectional view of the bowl body 511 with the opening facing upward, showing the pre-installed polishing agent 53 and the bleaching agent 63 which is added on top of the polishing agent 53 just before mixing. FIG. 13E shows the low pH bleaching agent 63 pre- installed in the syringe 60. The syringe 60 consists of a tubular body 61, a plunger piston 62 and a syringe output stopper 64.

To mix the dual agents, the plastic cover sheet 513 is removed from the dual-agent bowl 50; the syringe output stopper 64 is removed from the syringe body 61; the bleaching agent 63 is pressed out from the syringe 60 by the plunger piston 62 to added onto the polishing agent 53; the blending pins 414 at the output end of the mixing adaptor 40 are inserted into the bowl body 511; and the input-shaft 411 is inserted into the central chuck 2100 on the matching adaptor 21. The blending pins 414 rotate and mix the two agents thoroughly, resulting in the pH value of the mixture being properly titrated. The mixed paste is ready for immediate application to the teeth.

Figure 14:
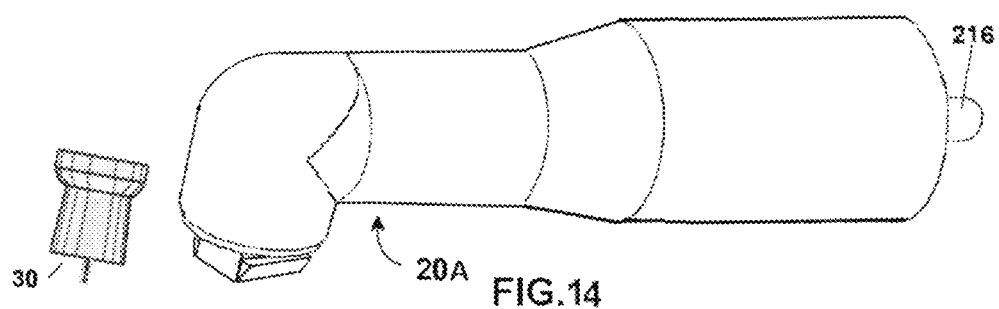
FIG. 14 is an isometric view of the swinging angle as shown in FIG. 2. With the rubber cup attached at the output end, the swinging angle by itself can be used as a prophylaxis angle with back-and-forth swinging output by using a powered driver in dental clinics.

FIG. 14 is an isometric view of the swinging angle 20A in FIG. 2. The figure also includes the attachable rubber cup 30. The swinging angle 20A with the attached rubber cup 30 as an assembly can be used by itself as a prophylaxis angle in dental clinics.

Figure 14A:
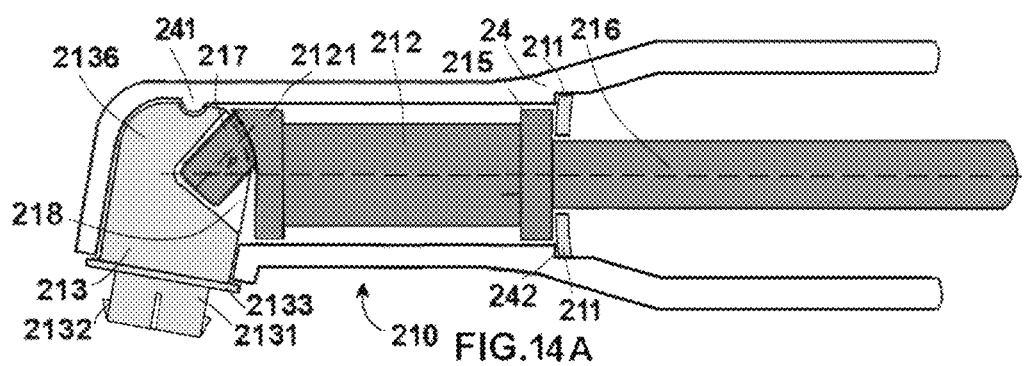
FIG. 14A shows the cross-sectional view of the swinging angle with the full-contact swinging mechanism in FIG. 3A.
Figure 14B:
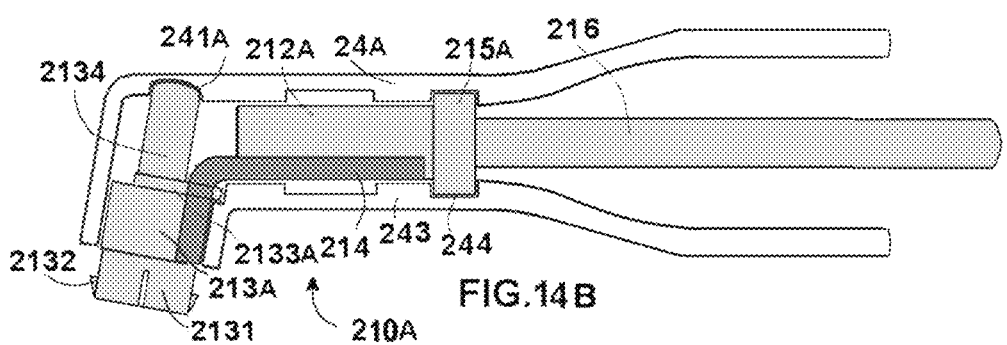
FIG. 14B shows the cross-sectional view of the alternative instance the bent-rod-swinging angle with the bent-rod-driving mechanism as in FIG. 3B.

As in FIG. 4, FIG. 14A shows the cross-sectional view of the tilted off-axis rod-swinging angle 210 with the full-contact swinging mechanism. As in FIG. 7, FIG. 14B shows the cross-sectional view of the alternative bent-rod-swinging angle 210A.

Figure 15:
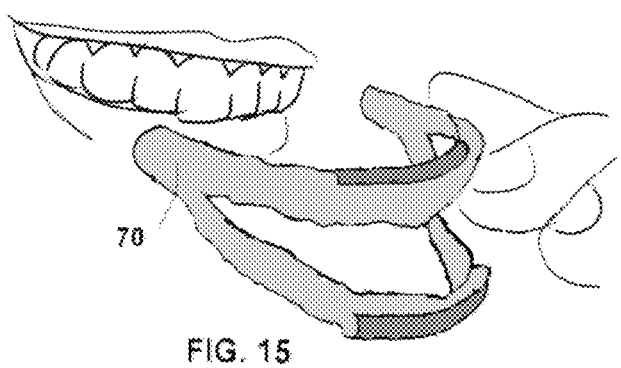
FIG. 15 illustrates a user-specific-formed thermoplastic gum cover being put into the user's mouth.
Figure 15A:
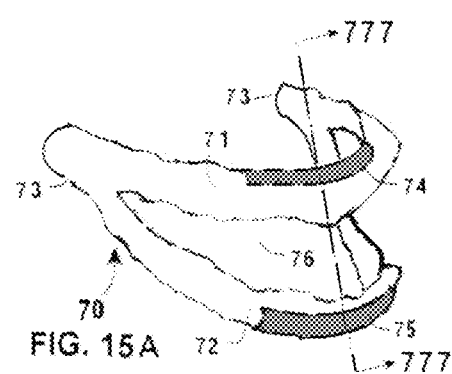
FIG. 15A describes the details of the gum cover. A pre-shaped gum cover is shown in FIG. 15B. It is softened in hot water and then reshaped in user's mouth to fit personally, as shown in FIG. 15A.

FIG. 15 illustrates a user inserting a user-specific-formed thermoplastic gum cover 70 (shown in FIG. 1) into the mouth. FIG. 15A describes the details of the user-specific-formed thermoplastic gum cover 70. FIG. 15A777 is a cross-sectional view from cutting plane 777-777 in FIG. 15A. The user-specific-formed thermoplastic gum cover 70 consists of the upper protection arch 71 and the lower protection arch 72 that are joined at the arch ends 73 to form the gum cover. The central upper and lower flange 74 and 75 protrude out from the central part of the upper and lower protection arch 71 and 72, respectively. A window frame 76 is formed by the gum cover.

Figure 15B:
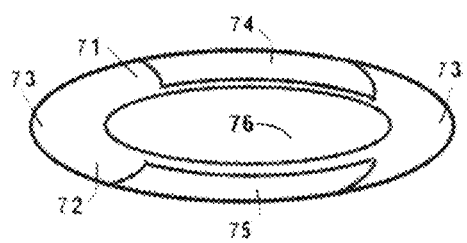
FIG. 15C is an isometric view of the pre-shaped thermo-plastic gum cover in FIG. 15B.
Figure 15C:
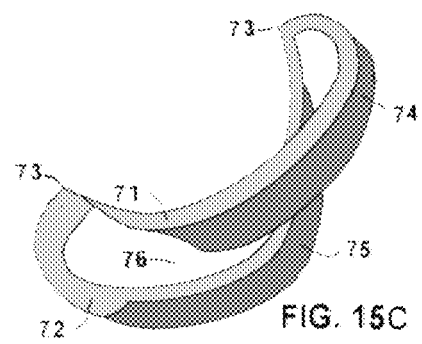
Figures 15A, 777:
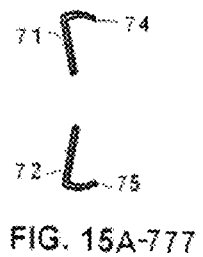

FIG. 15B is a frontal view of the pre-shaped thermoplastic polycaprolactone (PCL) gum piece before it is reshaped into the user-specific-formed thermoplastic gum cover 70 in FIG. 15A. FIG. 15C is and isometric view of the pre-shaped thermo-plastic gum cover shown in FIG. 15B.

When the pre-shaped thermo-plastic gum cover as shown in FIG. 15B is softened, e.g. in hot water, and then pressed on of the upper and lower front teeth of the user, the upper and lower protection arch 71 and 72 are reshaped to fit the user's teeth profile. The reshaped central upper and lower flanges 74 and 75 help open the mouth in a proper pose so that the front several teeth are exposed in the windows frame 76 for the treatment by the rubber cup 30. The user-specific-formed thermoplastic gum cover 70 can be removed, cleaned, and used repeatedly.

The objectives of the invention are achieved by the design as shown above. Although specific examples of the present invention and its application are set forth herein, they are not intended to be exhaustive or limiting of the invention. These illustrations and explanations are intended to acquaint others skilled in the art with the invention, its principles, and its practical applications, so that others skilled in the art may adapt and apply the invention in its numerous forms, as may best suit the requirements of a particular use.

I claim:

1. A portable tooth polishing and bleaching system for simultaneous tooth surface polishing and bleaching, comprising: (a) a handpiece that contains a motor, electronic circuits and user controls, (b) a detachable swinging angle, which couples with said handpiece, contains a full-contact swinging mechanism comprising a driver with a protruding tilted off-axis rod on a concave surface front and a shape-matched domed trunk with a receiving vertical side slot to convert a continuous rotational input to a back-and-forth swinging output, and (c) a disposable rubber cup which connects onto said swinging angle by a mortise-and-tenon joint to carry out said back-and-forth swinging movement to apply to tooth surfaces.

2. The portable tooth polishing and bleaching system of claim 1, wherein the handpiece comprsing: (a) said motor to provide a continuous rotational input, (b) said electronic circuits and user controls, and (c) a housing to encapsulate said motor, electronic circuits and user controls, and to couple with and stabilize said swinging angle.

3. The portable tooth polishing and bleaching system of claim 1, wherein said full-contact swinging mechanism comprises: (a) a driving shaft which has one end to accept said continuous rotational input and the other end that has said concave surface front with said tilted off-axis rod, (b) a driven rotor comprising said domed trunk whose shape matches with said concave surface front of said driving shaft, and said side slot vertically on said domed trunk, such that during operation, said tilted off-axis rod repeatedly pushes back and forth inside said side slot with full length contact of said tilted off-axis rod during the entire push stroke to transfer the continuous rotational input of said driving shaft to said back-and-forth swinging output, (c) an angled casing to cover said driving shaft and said driven rotor, wherein the axes of said driven rotor and said driving shaft form an obtuse angle to transfer said continuous rotational input into said back-and-forth swinging output in such an angled direction.

4. The portable tooth polishing and bleaching system of claim 3, wherein the driving shaft is constrained by a lock washer with external teeth that radially positions the input end of said driving shaft, when installed, by biting into the inner wall of said angled casing; wherein the output end of said driven rotor features a barbed square tenon of said mortise-and-tenon joint and an axial slit for compliance during installation of said rubber cup.

5. The portable tooth polishing and bleaching system of claim 4, wherein when operating said driving shaft makes one continuous revolution in one direction, said driven rotor makes a first swing forward motion followed by a second swing backward motion of equal swing angle and equal duration, wherein the width of said side slot in said driven rotor is slightly bigger than the diameter of said tilted off-axis rod such that said driven rotor halts momentarily when switching swinging directions, in turn reducing the impulse of the direction change.

6. The portable tooth polishing and bleaching system of claim 3, wherein the assembly of said driving shaft and driven rotor comprises a symmetrical shape and a symmetric slot to output an identical back-and-forth swinging movement of the driven rotor regardless the direction of rotational input from the said motor.

7. The portable tooth polishing and bleaching system of claim 3, wherein the input end features a rectangular mortise of said mortise-and-tenon joint such that, when attached to said drive rotor, the rotational axis of said rubber cup is co-linear with the rotational axis of said driven rotor, and the deformation of said mortise from a rectangular shape into a square shape creates a force that prevents rotational slippage in said back-and-forth swinging movement.

8. The portable tooth polishing and bleaching system of claim 3, wherein said driving shaft mates with a standard dental clinic powered driver which output a continuous rotation drive, and transfers through said full-contact swinging mechanism to said back-and-forth swinging movement for tooth prophylaxis. for tooth prophylaxis.

9. The portable tooth polishing and bleaching system of claim 1, wherein the rubber cup output end features a frustoconical shape, when in use, to hold a paste between the inner wall of the rubber cup frustum and the tooth surface for applying said back-and-forth swinging movement to the tooth surfaces for maximum retaining of said paste and heat generation.

* * * * *